(12) United States Patent
Ofei et al.

(10) Patent No.: US 12,325,679 B2
(45) Date of Patent: Jun. 10, 2025

(54) FERRITIC STEEL PARTS IN UREA PLANTS

(71) Applicant: STAMICARBON B.V., Sittard (NL)

(72) Inventors: Kirk Anguah Ofei, Eindhoven (NL); Alexander Aleida Antonius Scheerder, Roosteren (NL)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 18/621,755

(22) Filed: Mar. 29, 2024

(65) Prior Publication Data

US 2024/0262787 A1 Aug. 8, 2024

Related U.S. Application Data

(62) Division of application No. 18/069,690, filed on Dec. 21, 2022, now Pat. No. 12,084,406, which is a
(Continued)

(30) Foreign Application Priority Data

Jul. 5, 2019 (EP) .................................... 19184798

(51) Int. Cl.
C07C 273/04 (2006.01)
B01D 1/06 (2006.01)
(Continued)

(52) U.S. Cl.
CPC ............ C07C 273/04 (2013.01); B01D 1/065 (2013.01); B01D 3/346 (2013.01); B01J 19/0013 (2013.01);
(Continued)

(58) Field of Classification Search
CPC . B01D 1/00; B01D 1/06; B01D 1/065; B01D 3/00; B01D 3/34; B01D 3/343;
(Continued)

(56) References Cited

U.S. PATENT DOCUMENTS 3,807,991 A  4/1974 Gregory et al.
4,071,083 A  1/1978 Creusot-Loire
(Continued)

FOREIGN PATENT DOCUMENTS

CN  102099500 A  6/2011
EP  1195194 A1  4/2002
(Continued)

OTHER PUBLICATIONS

Compilation of Technical Exchange Data of Chemical Plant Materials between China and Japan, 1982. Publication date Aug. 31, 1982. Chemical Industry Society of China, Chemical Industry Press. Relevant pp. 162-166. Relevant claims 1-10. An English translation attached hereto.
(Continued)

Primary Examiner — Natasha E Young
(74) Attorney, Agent, or Firm — Leason Ellis LLP

(57) ABSTRACT

The application provides in an aspect a process for producing urea in a urea plant comprising a high pressure synthesis section comprising a reactor, wherein the process comprises reacting $NH_3$ feed and $CO_2$ feed under urea formation conditions in said reactor to form a urea synthesis solution comprising urea, water, carbamate and ammonia, wherein the process further comprises contacting a carbamate-containing liquid stream with an equipment part of said high pressure synthesis section that is made of a ferritic steel alloy.

17 Claims, 1 Drawing Sheet

Related U.S. Application Data division of application No. 17/624,716, filed as application No. PCT/NL2020/050438 on Jul. 3, 2020, now Pat. No. 11,746,084.

(51) Int. Cl.

| | | |
|---|---|---|
| *B01D 3/34* | (2006.01) | |
| *B01J 19/00* | (2006.01) | |
| *B01J 19/02* | (2006.01) | |
| *B22F 7/06* | (2006.01) | |
| *C07C 273/16* | (2006.01) | |
| *C22C 38/00* | (2006.01) | |
| *C22C 38/02* | (2006.01) | |
| *C22C 38/04* | (2006.01) | |
| *C22C 38/26* | (2006.01) | |
| *C22C 38/42* | (2006.01) | |
| *C22C 38/44* | (2006.01) | |
| *C22C 38/48* | (2006.01) | |

(52) U.S. Cl.
CPC .............. *B01J 19/02* (2013.01); *C07C 273/16* (2013.01); *C22C 38/001* (2013.01); *C22C 38/002* (2013.01); *C22C 38/02* (2013.01); *C22C 38/04* (2013.01); *C22C 38/26* (2013.01); *C22C 38/42* (2013.01); *C22C 38/44* (2013.01); *C22C 38/48* (2013.01); *B01J 2219/00081* (2013.01); *B01J 2219/0286* (2013.01); *B22F 7/064* (2013.01); *B22F 2301/35* (2013.01); *C21D 2211/005* (2013.01)

(58) Field of Classification Search
CPC ....... B01D 3/346; B01J 19/00; B01J 19/0006; B01J 19/0013; B01J 19/02; B01J 2219/00; B01J 2219/00049; B01J 2219/00051; B01J 2219/00074; B01J 2219/00076; B01J 2219/00081; B01J 2219/02; B01J 2219/025; B01J 2219/0277; B01J 2219/0286; B22F 3/00; B22F 3/12; B22F 3/14; B22F 3/15; B22F 7/00; B22F 7/06; B22F 7/062; B22F 7/064; B22F 2301/00; B22F 2301/35; C07C 273/00; C07C 273/04; C07C 273/14; C07C 273/16; C21D 2211/00; C21D 2211/001; C21D 2211/005; C22C 38/00; C22C 38/001; C22C 38/002; C22C 38/004; C22C 38/02; C22C 38/04; C22C 38/18; C22C 38/20; C22C 38/22; C22C 38/26; C22C 38/40; C22C 38/42; C22C 38/44; C22C 38/48; F28F 1/00; F28F 1/003; F28F 21/00; F28F 21/08–083; Y02P 20/00; Y02P 20/141
See application file for complete search history.

(56) References Cited

U.S. PATENT DOCUMENTS

| | | |
|---|---|---|
| 4,444,731 A | 4/1984 | Knoki et al. |
| 2006/0073086 A1 | 4/2006 | Sakai et al. |
| 2008/0093064 A1 | 4/2008 | Gianazza et al. |
| 2009/0062566 A1 | 3/2009 | Kojima |
| 2011/0110812 A1 | 5/2011 | Hiraide et al. |
| 2012/0097378 A1 | 4/2012 | Gianazza et al. |
| 2012/0282149 A1 | 11/2012 | Mennen et al. |
| 2013/0121868 A1 | 5/2013 | Gandy et al. |
| 2013/0129560 A1 | 5/2013 | Matsuhashi et al. |
| 2014/0069619 A1 | 3/2014 | Hiraide et al. |
| 2016/0115562 A1 | 4/2016 | Santacreu et al. |
| 2018/0195157 A1 | 7/2018 | Ruffini et al. |
| 2018/0304224 A1 | 10/2018 | Larsson et al. |
| 2019/0330724 A1 | 10/2019 | Nishiyama et al. |

FOREIGN PATENT DOCUMENTS

| | | |
|---|---|---|
| EP | 2801396 A | 11/2014 |
| EP | 2813594 A1 | 12/2014 |
| EP | 3153599 A1 | 12/2014 |
| GB | 1333544 A | 10/1973 |
| JP | S45-038812 | 12/1970 |
| JP | S47-018831 | 9/1972 |
| JP | S57140643 | 8/1982 |
| JP | 2008045739 | 2/2008 |
| JP | 2012036444 | 2/2012 |
| JP | 2012112025 A | 6/2012 |
| JP | 2012526259 | 10/2012 |
| JP | 2012214881 | 11/2012 |
| JP | 2018168415 A | 11/2018 |
| WO | 9500674 A1 | 1/1995 |
| WO | 9950610 A1 | 10/1999 |
| WO | 2006/118071 | 12/2008 |
| WO | 2017013180 A1 | 1/2017 |
| WO | 2017014632 A1 | 1/2017 |
| WO | 2018003941 A1 | 1/2018 |

OTHER PUBLICATIONS

International Search Report and Written Opinion in corresponding International Patent Application No. PCT/NL2020/050438 mailed Aug. 31, 2020. 12 pages.
Meessen, Ullmann's Encyclopaedia, chapter Urea, 2010. 39 pages.
G. Notten, Corrosion Engineering Guide, KCI Publishing 2008, chapter 2. 38 pages.
Office Action for corresponding Chinese Application No. 202080048382.9 and English translation, dated Oct. 14, 2022.

FERRITIC STEEL PARTS IN UREA PLANTS

CROSS-REFERENCE TO RELATED PATENT APPLICATIONS

This application is a Divisional Application of Ser. No. 18/069,690, now U.S. Pat. No. 12,084,406, filed on Dec. 21, 2022, which is a Divisional Application of Ser. No. 17/624, 716, now U.S. Pat. No. 11,746,084, filed on Jan. 4, 2022, which is a U.S. National Stage Application under 35 U.S.C. § 371 of International Patent Application No. PCT/NL2020/050438, now Wo 2021/006729, filed Jul. 3, 2020, which claims the benefit of priority of European Patent Application No. 19184798.7 filed Jul. 5, 2019, all of which are incorporated by reference in their entireties.

FIELD

The present invention pertains to a process for producing urea, a high pressure stripper for a urea plant, a use of ferritic stainless steel, a method of manufacturing a component, a heat exchanger tube, and an apparatus comprising a compound steel tube. Also described is a urea plant which comprises an equipment part comprising certain steel alloys.

INTRODUCTION

Urea is commercially produced by the reaction of $CO_2$ and $NH_3$ to form ammonium carbamate and the dehydration of the carbamate to urea and water to give a urea synthesis solution. The urea synthesis solution comprises urea, water, ammonium carbamate, and ammonia. The intermediate product ammonium carbamate is extremely corrosive, at least at the higher temperatures typically applied in the high pressure synthesis section of a urea plant. The corrosiveness of the synthesis solution has forced urea manufacturers to set very strict demands on the quality and composition of construction materials, in particular to have a sufficiently long lifetime of the high pressure equipment.

It is known that austenitic stainless steel exposed to carbamate-containing solutions involved in urea synthesis can be kept in a passivated (non-corroding) state by a given quantity of oxygen, for instance by introducing passivation air into the high pressure synthesis section (Ullmann's Encyclopedia, chapter Urea, 2010). The passivation is provided by the formation of a protective chromium oxide layer. However, the oxide layer may slowly dissolve in hot carbamate solution.

Generally, corrosion systems of passivating metals can be analysed using polarization curves. In a first case, the cathodic polarization curve has only one stable intersection curve with the anodic polarization curve of the metal. This is for instance typical of stainless steel in acid solutions containing oxidizers. In a second case, the anodic polarization curve and the cathodic polarization curve has three intersection points at different potentials, one of which is unstable, one of which is in the active region and the other in the passive region. Stainless steels in oxygen carbamate solutions are typical for this behaviour. In a third case, there is only one intersection point, which is in the active region and high corrosion rate occurs. This case is characteristic for stainless steel in air-free carbamate solutions (G. Notten, Corrosion Engineering Guide, KCl Publishing 2008, para. 2.4.5).

The use of passivation air has the disadvantage that for a given absolute pressure in the reactor (fixed by reactor design) the partial pressure of $NH_3$ and $CO_2$ becomes lower due to the inerts in the reactor, thereby decreasing the boiling temperature of the liquid reaction medium, at which the reactor operates, such that conversion is decreased. In addition the effective volume of the reactor is decreased by inerts. Furthermore passivation air ends up in the inerts gas stream to be vented from the synthesis section which requires ammonia removal from the inerts, such that more passivation air increases $NH_3$ and $CO_2$ recycle as medium pressure or low pressure carbamate solution, which is disadvantageous.

Ammonia emissions are problematic for environmental reasons and as loss of feedstock. In order to avoid the formation of explosive mixtures after scrubbing of the inerts, hydrogen may have to be removed from the $CO_2$ feed upstream of the synthesis section.

Temperature is an important factor in the corrosion behaviour of the steels employed in urea synthesis. For instance, a passivating oxide layer may be less stable at higher temperatures. Polarization curves are also dependent on temperature.

In the urea production processes of the stripping type, the heat-exchanging tubes in the high pressure stripper are considered to usually represent the most critical place with respect to danger of corrosion, due to the combination of high temperatures, high carbamate content, and low oxygen partial pressure in these tubes.

A stripper is a costly equipment piece and a long lifetime is of great importance. The lifetime is typically limited by corrosion, especially in the heat exchanger tubes. Furthermore, replacing, repairing or plugging tubes is costly, also in terms of plant downtime, and introduces risks of unstable operation. Hence, stripper maintenance is desirably minimized. Furthermore a demonstrated lower corrosion rate allows for reducing the frequency of mandatory inspections of plant equipment thereby increasing plant uptime. A low corrosion rate is also important to achieve the desired very high reliability of the stripper equipment and to achieve a high on stream factor and to reduce the number of unwanted shutdowns.

In urea plants of the $CO_2$ stripping type, the austenitic steel UNS S31050 (25Cr-22Ni-2Mo) has been used for a long time and typically requires at least 0.6 vol. % passivation oxygen added as air.

In the 1990's duplex austenitic-ferritic steel alloys were introduced as materials of construction in urea plants.

In the art, duplex stainless steels are called "duplex" because they have a two-phase microstructure consisting of grains of ferritic and austenitic stainless steel.

In urea plants of the Stamicarbon $CO_2$ stripping type, a duplex steel alloy as described in WO 95/00674 can be used in the high pressure synthesis section. Such steel is commercially sold under the trademark Safurex® which is a super duplex steel, also known as UNS S32906. The use of this super duplex steel alloy allowed reducing the level of passivation oxygen by 50% giving an amount of added passivation air of 0.3 vol % oxygen relative to the $CO_2$ feed or to even lower levels such as 0.1 vol %. This alloy can be used for all high pressure equipment in the urea plant, especially for the parts (e.g. lining, piping) exposed to hot carbamate, i.e. in the HP synthesis section. The overall passive corrosion rate is reported as less than 0.01 mm per year on stream (i.e. in operation); however in in certain vertical parts of the stripper tubes, which are exposed to the highest temperatures in operation, passive corrosion rates up to 0.09 mm per year on steam have been observed.

Further suitable duplex steel alloys are described in WO 2017/013180 and WO 2017/014632 also published as US 2018/195158 which both describe a duplex stainless steel alloy with low passive corrosion rates in carbamate environments at higher temperature, e.g. higher than 200° C. This alloy is particularly suitable for the stripper tubes.

In urea plants with ammonia-stripping or self-stripping (Snamprogetti process), for a long time the stripper tubes were made of titanium. Later bimetallic tubes were used. These tubes consist of two coaxial tubes, an external tube made of an austenitic stainless steel and an internal tube made of Zr. More recently full Zr tubes are used, and tubes obtained by extrusion of titanium (external) and zirconium (internal) billets.

SUMMARY

Accordingly, the invention relates in a first aspect to a process for producing urea in a urea plant comprising a high pressure synthesis section comprising a reactor, wherein the process comprises reacting $NH_3$ feed and $CO_2$ feed under urea formation conditions in said reactor to form a urea synthesis solution comprising urea, water, carbamate and ammonia, wherein the process further comprises contacting a carbamate-containing liquid stream with an equipment part of said high pressure synthesis section that is made of a ferritic steel alloy. The ferritic steel alloy preferably comprises in wt. %:
C max. 0.005
Si 0.1 to 0.4
Mn max. 0.4
P max. 0.020
S max. 0.020
Cu max. 0.25
Ni max. 0.50
Cr 20.0 to 35.0
Mo 0.75 to 1.50
N 0.0050 to 0.0125
Nb 0.060 to 0.375
balance Fe, max. 0.50 wt. % total added processability elements, and impurities, and wherein preferably the amount of Nb in wt. % meets the following equation $12*(wt. \% N) < Nb < 30*(wt. \% N)$ (Preferred Alloy Composition 1).

Preferably, the ferritic steel alloy comprises in wt. %:
C max. 0.0030
Si 0.1 to 0.3
Mn max. 0.2
P max. 0.020
S max. 0.020
Cu max. 0.25
Ni max. 0.20
Cr 25.0 to 27.5
Mo 0.75 to 1.50
N 0.0050 to 0.0125
Nb 0.060 to 0.375
balance Fe and unavoidable occurring impurities; and wherein the amount of Nb in wt. % meets the following equation $12*(wt. \% N) < Nb < 30*(wt. \% N)$ (Preferred Alloy Composition 2).

Preferably, the amount of Nb meets the equation $15*(wt. \%) N < Nb < 25*(wt. \% N)$ (Preferred Alloy Composition 3).

Generally, the equipment part has a purely ferritic micro structure. Hence, the equipment part has a one-phase ferritic micro structure. This applies to all ferritic steel alloys as used herein and provides for a difference with duplex stainless steel alloys.

The invention further pertains to a high pressure stripper for a urea plant, wherein the stripper is a shell-and-tube heat exchanger comprising tubes, a shell, and an upper tube sheet and a lower tube sheet, wherein the stripper is a falling-film type vertical shell-and-tube heat exchanger, wherein the stripper comprises an inlet for receiving urea solution further comprising carbamate in the tubes at an upper part of the tubes and wherein the stripper comprises an inlet for receiving steam in the shell space between the shell and the tubes and the two tube sheets, wherein the tubes comprise at least a part which is made of ferritic steel and which is in operation in contact with said urea solution comprising carbamate. Preferably the tube parts have a purely ferritic micro structure.

The invention also pertains to the use of a ferritic stainless steel in ammonium carbamate environment, said use comprising exposing the steel to a fluid comprising ammonium carbamate.

The invention also pertains to a method of manufacturing a component, wherein the component comprises a first and a second part which have a metallurgical bond to each other, wherein the first part is made of ferritic stainless steel, and the second part is for instance made of a different type of steel than the first part, the method comprising:
 i) providing a mold defining the shape of an object to be manufactured:
 ii) filling a portion of the mold corresponding to said first part with first stainless steel alloy powder which is a ferritic stainless steel alloy powder;
 iii) filling a portion of the mold corresponding to said second part with a second stainless steel alloy powder having a different elemental composition than said first stainless steel alloy powder:
 iv) subjecting said mold, as filled with said first and second stainless steel alloy powder to hot isostatic pressing (HIP), to give a consolidated object.

The invention also pertains to a heat exchanger tube, wherein the heat exchanger tube is a bimetallic tube comprising an inner tube layer and outer tube layer, wherein the inner tube layer is made of a ferritic steel alloy and the outer tube layer is made of a material selected from the group of duplex stainless steel, titanium, titanium alloys, zirconium, zirconium alloys and austenite stainless steel.

The invention also pertains to an apparatus comprising:
 at least one steel tube
 at least one holder element comprised by a steel having a duplex austenite-ferrite microstructure or purely austenitic microstructure, wherein the steel tube penetrates the holder element and is attached to the holder element by means of a weld joint provided on an outer surface of the tube and on the holder element,
 the apparatus being characterized in that
 the steel tube is a compound tube, comprising an inner tube part which has a purely ferritic microstructure, and an outer tube part which has a duplex austenite-ferrite microstructure or purely austenitic microstructure.

For example, the ferritic steel alloy as used in the invention has a purely ferritic micro structure. Hence, the steel for instance has a one-phase ferritic micro structure. In particular, the ferritic steel alloy as used herein is not a duplex ferritic-austenitic stainless steel.

DETAILED DESCRIPTION

Figure 1:
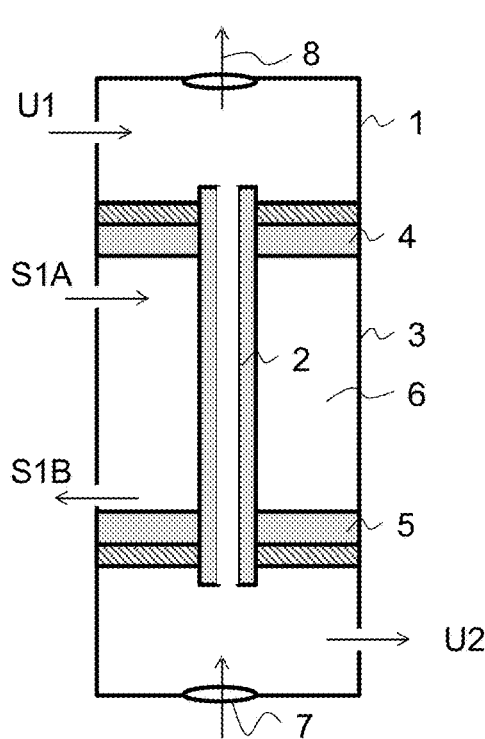
FIG. 1 schematically illustrates an example stripper according to the invention.

In a first aspect, the invention is broadly based on the judicious insight that the ferritic steel alloys with the mentioned elemental compositions, in particular with preferred alloy compositions 1-3, which include Nb, can be used in the high pressure section of a urea synthesis plant for the equipment parts which during operation are in contact with the carbamate-containing solutions, such as urea synthesis solution, while providing for a very high degree of resistance against the corrosion as caused by carbamate. Equipment parts with these elemental compositions have a purely ferritic micro structure.

These ferritic steels as such are described in U.S. Pat. No. 3,807,991 to Gregory. Therein the corrosion resistance results are given as measured by exposure to ferric sulfate—50% sulfuric acid according to ASTM A262-70. However, as discussed in US 2018/195158A1, para. [0027], the results from conventionally used corrosion tests, such as the Streicher test with ferric sulfate-sulfuric acid test solution which are performed at 127° C., do not correlate to with the actually observed corrosion in the specific equipment (stripper tube) in urea plants. In particular, corrosion rates are environment specific. Furthermore the cathodic polarization curves of acidic solutions with oxidizers are different from the cathodic polarization curves of steel alloys in carbamate solutions.

The present inventors have found that the mentioned types of ferritic steel alloys provides for excellent corrosion resistance in a high pressure autoclave with ammonium carbamate thereby simulating process conditions without added passivation air. The results are given in Example 1 below and demonstrate especially the very low rate of passive corrosion.

Thereby, the present invention makes available these ferritic steels for use in a high pressure synthesis section of urea plants, and in particular for stripper tubes.

The invention pertains in a first aspect to a urea production process wherein a carbamate-containing liquid stream is contacted with an equipment part that is made of a ferritic steel alloy which comprises, preferably consists of, in weight %:

C max. 0.005; preferably max. 0.0030
Si 0.1 to 0.4; preferably 0.1 to 0.3
Mn max. 0.4; preferably max. 0.2
P max. 0.020
S max. 0.020
Cu max. 0.25
Ni max. 0.50; preferably max. 0.20
Cr 20.0 to 35.0; preferably 25.0 to 27.5
Mo 0.75 to 1.50
N 0.0050 to 0.0125
Nb 0.060 to 0.375
balance Fe and unavoidable occurring impurities, and wherein the amount of Nb in wt. % meets the following equation $12*(\text{wt. \% N}) < \text{Nb} < 30*(\text{wt. \% N})$.

Hence, the amount of Nb is, on weight basis, 12 to 30 times the amount of nitrogen.

The preferred ranges for C, Si, Mn, Ni and Cr can be used independently and in combination. Preferably, the amount of Nb meets the equation $15*(\text{wt. \%}) \text{ N} < \text{Nb} < 25*(\text{wt. \% N})$. In a preferred embodiment, C, Si, Mn, Ni and Cr have all the mentioned preferred ranges, more preferably furthermore Nb meets the equation $15*(\text{wt. \%}) \text{ N} < \text{Nb} < 25*(\text{wt. \% N})$.

The low levels of C and N can be achieved for instance with vacuum refining. The low level of C can be obtained for example using argon oxygen decarburization. In addition, for instance electron beam refining of the melt in vacuum can be used. The content N is desirably as low as possible. A level of e.g. 50 ppm (by weight) N is for instance used. In some embodiments N can be lower and in some embodiments the steel alloy comprises N max. 125 ppm by weight. Without wishing to be bound by way of theory, the presence of Nb may help to prevent the precipitation of any C or N as Cr nitrides or Cr carbides. In this way the formation of zones with low Cr available for passivation at the grain boundaries is avoided and intergranular corrosion is prevented. This contributes to the extremely low levels of passive corrosion rates upon contact with ammonium carbamate solutions.

When the term "max." is used, the skilled person knows that the lower limit of the range is 0 wt. % unless another number is specifically stated. Hence for C, Mn, Cu, P, S, and Ni, the lower limit is 0 wt. %, as they are optional components. These elements can be present in the ferritic steel alloy as specifically added or as contamination with a controlled maximum level as specified.

Ferritic steel grades having the recited compositions are described as such in U.S. Pat. No. 3,807,991 to Gregory.

In the ferritic steels according to the present invention, Cr is used at 20.0 to 35.0 wt. %, preferably 25.0 to 27.5 wt. % to provide corrosion resistance. Cr may act as ferrite former in the steel.

Mo is used at 0.75 to 1.50 wt. %, preferably 0.75 to 1.50 wt. % to provide further improved corrosion resistance. Mo is also a ferritic stabilizing element.

Si can be used as deoxidation additive during manufacture. Si is also a ferritic stabilizing element.

Mn is an optional element with amount max. 0.4 wt. %, preferably max. 0.2 wt. %.

Sulfur (S) can influence the corrosion resistance negatively. Therefore, the content of S should be restricted to max. 0.020 wt. %, such as max. 0.010 wt. %.

Phosphorus (P) is a common impurity element. If present in amounts greater than approximately 0.020 wt. %, it can result in adverse effects on e.g. mechanical properties. The amount of P in the alloy should be restricted to max. 0.020 wt. %, such as max. 0.010 wt. %.

The Cu content should be kept low. Hence, Cu is max. 0.25 wt. %.

The steel alloy is a ferritic steel alloy and hence Ni is max. 0.50 wt. %, preferably max. 0.20 wt. %. Ni is considered an austenite forming element.

The balance in the ferritic steel is Fe, max. 0.50 wt. % in total of processability elements, and (unavoidable occurring) impurities. Examples of unavoidable impurities are elements and compounds which have not been added on purpose, but cannot be fully avoided as they normally occur as impurities in e.g. the material used for manufacturing the ferritic steel. For instance scrap metal may be used as source for Fe in the steel. The optionally used, max. 0.50 wt. % in total, processability elements are metal elements which are added for processability.

The preferences for the ferritic steel alloy composition as discussed above apply for the ferritic steels of all aspects of the present invention.

It is indeed surprising that a ferritic steel alloy with the mentioned composition shows a high level of corrosion resistance against ammonium carbamate as it is generally considered that ferritic steels are unsuitable. Without wishing to be bound by theory, the inventors believe that the very low levels of C and Ni in combination with the very low level of N, balanced out by the addition of Nb and Mo, act together to prevent austenite formation and chromium nitrides and chromium carbides. It is known that in ferritic/austenitic duplex steels nickel plays an important role in ensuring corrosion resistance in ammonium carbamate environments.

In the present application, the term "ferritic steel alloy" is used as distinct from "ferritic-austenitic duplex steel alloy" in that the former has a purely ferritic micro structure whereas duplex stainless steels do not have a purely ferritic micro structure.

The invention also pertains to a process for producing urea in a urea plant, and also to such a urea plant. The urea plant comprises a high pressure synthesis section comprising a reactor. The process comprises reacting $NH_3$ feed and $CO_2$ feed under urea formation conditions in the reactor to form a urea synthesis solution comprising urea, water, carbamate and ammonia, wherein the process (further) comprises contacting a carbamate-containing liquid stream with an equipment part of said high pressure synthesis section that is made of a ferritic steel alloy with the mentioned composition. In some embodiments, said contacting and said reacting are one and the same step and the reactor comprises said equipment part. Hence, the urea production process comprises reacting $NH_3$ feed and $CO_2$ feed under urea formation conditions in the reactor to form a urea synthesis solution and involves contacting a carbamate-containing liquid stream with an equipment part, wherein said equipment part is comprised in said high pressure synthesis section, and wherein said equipment part is made of a ferritic steel alloy, preferably a ferritic steel alloy with the mentioned composition, more preferably with preferred alloy compositions 1-3 described herein. The equipment part in particular has a purely ferritic micro structure. The carbamate component of said liquid stream originates from said urea formation reaction in said reactor.

The carbamate-containing liquid stream is for instance the urea synthesis solution which also contains carbamate, or a carbamate recycle stream. The carbamate-containing liquid stream comprises e.g. 15 wt. % to 95 wt. % carbamate, such as 45 wt. % to 95 wt. % carbamate, and may for example further comprise 10 wt. % or more, and/or less than 50 wt. % urea, and for instance water in an amount of e.g. more than 1 wt. % and/or less than 20 wt. %. The carbamate-containing liquid stream is for instance at 180° C., such as more than 200° C. The carbamate-containing liquid stream is for instance a solution of carbamate, wherein e.g. water is the solvent.

The process for instance comprises decomposing carbamate from the urea synthesis solution to give a gas stream comprising $NH_3$ and $CO_2$, and condensing said gas stream to give a liquid stream comprising carbamate, and typically water, which is recycled to the urea synthesis section. The decomposition is for instance carried out at medium pressure and/or low pressure, and for instance also in a high pressure stripper which is part of the synthesis section.

In a preferred embodiment, the high pressure synthesis section comprises a stripper and the process comprises subjecting the urea synthesis solution to a stripping step in said stripper. Preferably, independently of the design of the stripper, the stripping step comprises subjecting the urea synthesis solution at high pressure to heating and simultaneous counter-current contacting the solution with a gas stream, wherein the gas stream has a lower partial vapor pressure for $NH_3$ and/or for $CO_2$. The gas stream is for instance $NH_3$ feed, $CO_2$ feed, or obtained by the downstream vaporization of the urea synthesis solution. The stripping step involves promoting the decomposition of ammonium carbamate in the liquid phase into $NH_3$ and $CO_2$ and the transfer of $NH_3$ and $CO_2$ from the liquid phase into the gas phase. The solution is usually supplied over a wall surface during the stripping (which wall is used for heat transfer and is for instance a tube wall). Preferably at least this wall part is made of the ferritic steel as described. Preferably the solution is provided as a falling film during the stripping, more preferably in a stripper tube. In principle any kind of heating can be used, for instance with a heating medium such as steam.

Preferably the stripper is a shell-and-tube heat exchanger comprising tubes. Preferably the stripper tubes are in part made of the mentioned ferritic steel alloy. More preferably at least the part of the tubes forming the inner surface of the tube is made of the mentioned ferritic steel alloy. Preferably the process comprises passing a urea solution comprising carbamate through the stripper tubes thereby contacting it with parts of the stripper tubes made of the mentioned ferritic steel alloy, and preferably heating the tubes, such as by supplying heating medium, such as steam. In some embodiments the tubes are entirely made of the ferritic steel alloys. In some embodiments the parts providing the inner surface, which in operation is in contact with carbamate, is made of the mentioned ferritic steel.

Preferably, the process comprises operating the stripper as vertical falling-film shell-and-tube heat exchanger and involves maintaining a falling film of the urea solution (also comprising carbamate) in the tubes. Preferably the method comprises supplying strip gas to the bottom of the tubes. Preferably the strip gas is $CO_2$ feed. Preferably at least 50 wt. % or at least 75 wt. % or even at least 90 wt. % of the $CO_2$ feed for the urea production is supplied as strip gas to the stripper. Alternatively, $NH_3$ can be used as strip-gas. In some embodiments, self-stripping can also be used as is well-known in the art. In case of self-stripping, a molar ratio of $NH_3$ to $CO_2$ (N/C ratio; based on theoretical initial mixture) of at least 3.2, typically 3.2-3.4 is used in the reactor and the excess $NH_3$ is used as strip gas by heating of the synthesis solution. In self-stripping and ammonia stripping, generally higher temperatures are used than for $CO_2$ stripping making the corrosive effect of carbamate even more severe. Hence, for self-stripping and ammonia stripping the present invention is particularly advantageous.

The stripping process typically involves counter-current contact between the strip gas and the urea solution comprising carbamate in the stripper tubes, in particular with a falling film of urea solution and upward flow of gas. The stripper is usually a shell-and-tube heat exchanger and preferably has an inlet for solution and an outlet for gas at the top and an outlet for stripped solution at the bottom, and in case of $CO_2$ stripping and ammonia stripping an inlet for strip gas at the bottom (these inlets and outlets are all for the tube side). Preferably in the shell side steam is supplied from an inlet that is arranged higher than the outlet for condensate to provide for flow of steam co-current with the urea solution in the tubes. In the stripping step, which includes heating, at least a part of the carbamate in the urea solution is decomposed to give $CO_2$ and $NH_3$ which is stripped off, the mixed gas from the stripper is supplied to a HP carbamate condenser where it is condensed to carbamate. The carbamate from the HP carbamate condenser is recycled to the reactor. Optionally, the condenser and reactor are combined in one vessel, for example a pool reactor. Already some urea may be formed in the HP carbamate condenser. The HP carbamate condenser is e.g. a shell-and-tube heat exchanger, is e.g.

a horizontal condenser, and is e.g. configured for receiving cooling fluid in the tubes and gas to be condensed at the shell side.

The decomposition of carbamate is an endothermic reaction and hence the stripping involves heating the urea solution. In a preferred embodiment, the temperature in at least part of the stripper tube is above 200° C., or even at least 205° C., and in particular in this part the mentioned ferritic steel alloy can be used. The mentioned temperatures are e.g. skin temperatures at the inner surface of the tubes. In principle any kind of heating can be used.

In one embodiment, the stripping is based on self-stripping and is carried out at a temperature of at least 200° C., preferably in the range 200-210° C. as temperature of the stripper bottom. Such temperatures are typical for self-stripping. Conventional view is that at such high temperatures, stainless steel is not suitable as construction material for the stripper from a corrosion point of view; titanium and other materials are used instead (Ullmann's Encyclopedia, Urea, 2010). Surprisingly it was found that the ferritic steel alloys as mentioned can be used for the tubes of strippers operating at such temperatures and e.g. according to the self-stripping principle.

Without wishing to be bound by way of theory, the equipment part made of the mentioned ferritic steel alloy has in operation a passivating layer of chromium oxide. Without wising to be bound by way of theory, the passivating layer can be formed e.g. during manufacture or installation of the equipment. For instance the layer forms spontaneously upon contact with air and water vapor.

In a preferred embodiment, an oxygen fraction contained in the $CO_2$ feed is advantageously used for maintaining the passivating layer during the lifetime of the equipment part even in the absence of passivation air being added to the $CO_2$ feed. The $CO_2$ feed may for instance be obtained from a syngas production process. The syngas production process may for instance provide $H_2$ which is reacted with $N_2$ to $NH_3$ in an ammonia plant, wherein the formed $NH_3$ is used at least in part as feed for the urea synthesis. The syngas production process comprises for instance steam methane reforming with downstream water gas shift reaction, or another process which converts hydrocarbon into a reaction mixture containing $CO_2$ and $H_2$. The steam reforming, if used, comprises for instance primary reforming with downstream secondary reforming. The secondary reforming involves for instance autothermal reforming with added oxygen. Generally, the reaction mixture also includes some $O_2$. The $CO_2$ is for instance separated from the reaction mixture, for instance using absorption in an absorption medium and desorption. The separated stream, e.g. the desorbed gas stream, may contain $O_2$ in addition to $CO_2$. In a preferred embodiment, the level of $O_2$ is controlled above a certain minimum level.

For example, the concentration of oxygen in the synthesis section is less than 5 ppm, less than 3 ppm, less than 1 ppm, less than 0.50 ppm or less than 0.10 ppm by weight relative to total process fluids in the synthesis section. The concentration of oxygen in the synthesis section is for instance above 10 ppb by weight relative to total process fluids in the synthesis section.

Preferably, no passivation air is added to the synthesis section.

Accordingly, in a preferred embodiment, the urea production process furthermore comprises obtaining said $CO_2$ feed by separating $CO_2$ from a first gas stream comprising $CO_2$ and $O_2$, wherein the amount of oxygen present in the high pressure synthesis section of the urea plant is for at least 50 mol. % or at least 90 mol. % derived from said first gas stream. The first gas stream is from instance the reaction mixture from a syngas production processes, comprising for instance steam methane reforming as discussed. The feature that the oxygen present in the HP synthesis section of the urea plant comes for at least 50 mol. % or at least 90 mol. % from that first gas stream indicates that no large amounts of oxygen or air are added to the $CO_2$ feed or introduced to the HP synthesis section. In this way advantageously the oxygen already present from the $CO_2$ production in an upstream process, e.g. the syngas production, is used for maintaining the ferritic steel of the components, in particular of the stripper tubes in the passivated state.

The stripped urea solution is for instance supplied to a recovery section at medium or low pressure where further carbamate is decomposed and ammonia is removed in a decomposer to give purified urea solution and a gas stream which is condensed in a condenser to give carbamate solution. The carbamate solution is pumped back to the high pressure synthesis section. The purified urea solution is e.g. supplied to an evaporation section comprising vacuum evaporators for removal of water to give a urea melt. Water vapor from the evaporators is typically condensed and the condensate is typically supplied to a waste water treatment section comprising a urea hydrolysis unit and a desorber to give cleaned waste water and a stream comprising $CO_2$ and $NH_3$ which can be recycled to the urea synthesis section. The urea melt from the evaporation section is e.g. supplied to a finishing section where it is solidified to a solid urea product, e.g. with granulation or prilling. The purified urea solution can also be used, e.g. after appropriate dilution, for instance for making DEF (Diesel Exhaust Fluid), e.g. according to ISO1 22241-4:2009 which sets purity levels and in particular specifies maximum metal contents. DEF must have very low metal contents. Low metal contents are also desirable for other types of liquid and solid urea products. In order to achieve low metal contents a low corrosion level is important because corrosion may introduce metallic ions into the process streams.

The invention furthermore pertains to a high pressure stripper.

FIG. 1 schematically illustrates a non-limiting example of such a high pressure stripper. The stripper (1) is a stripper for a urea plant, and is a shell-and-tube heat exchanger and comprises tubes (2), a shell (3) and an upper tube sheet (4) and a lower tube sheet (5). The tubes are arranged in a tube bundle. In practice, the tube bundle may contain e.g. more than 1000 tubes or more than 2000 tubes, e.g. 3000 to 5000 tubes or even more. The stripper is, or is configured for operation as, a falling-film type vertical shell-and-tube heat exchanger with an inlet for receiving urea solution comprising carbamate (U1), such that this solution is received in the tubes at an upper part of the tubes in operation. The stripper further comprises an inlet for receiving steam (S1) in the shell space (6) between the shell (3) and the tubes (2) and the two tube sheets. The tubes comprise at least a part that is made of the mentioned ferritic steel and that is in operation in contact with said urea solution (U1) which also comprises carbamate. Hence, at least part, preferably all, of the inner tube surface is provided by the mentioned ferritic steel, having the elemental composition as describes, for example an elemental composition according to preferred alloy compositions 1-3.

Hence, the stripper has an inlet for urea solution (U1), an outlet for stripped urea solution (U2), both in liquid communication with the tubes; as well as an inlet for steam (S1A) and an outlet for condensate and possibly some steam (S1B) both in fluid communication with the shell space (6). The outlet (S2) is arranged lower than the inlet (S1) and above and near to the lower tube sheet (5). In case of a $CO_2$ stripper, the stripper comprises an inlet (7) for $CO_2$ feed used as strip gas into the bottom of the tubes. The stripper further comprises at the top an outlet (8) for mixed gas.

The tubes are heat exchanging tubes for indirect heat exchange between the steam and the urea solution. In addition counter-current contact between strip gas and urea-solution occurs in the tubes.

The upper tube sheet (4) preferably comprises a pressure-bearing inner part made of carbon steel and an overlay of corrosion resistant steel. The overlay is provided at the upper tube sheet side. The overlay is for instance made of duplex stainless steel.

The lower tube sheet (5) preferably comprises a pressure-bearing inner part made of carbon steel and an overlay of corrosion resistant steel. The overlay is provided at the bottom tube sheet side. The overlay is for instance made of duplex stainless steel.

The invention also pertains to a urea plant comprising a high pressure section comprising an equipment part comprising the mentioned ferritic steel. The urea plant comprises for instance a stripper as described. The stripper comprises the tubes comprising the parts made of the mentioned ferritic steel.

For example, the invention pertains to a urea plant comprising a high pressure section comprising a reactor, a stripper (preferably as described) and a HP carbamate condenser, and optionally a scrubber, wherein the reactor has an outlet for liquid connected to an inlet of the stripper, wherein the stripper has an outlet for liquid and an outlet for gas, wherein the outlet for gas of the stripper is connected to an inlet of the condenser, wherein the condenser has an outlet for liquid connected to an inlet of the reactor, and wherein the synthesis section has an inlet for $CO_2$ feed and an inlet for $NH_3$ feed, as well as an inlet for a carbamate stream. The reactor has an outlet for gas that is optionally connected with an inlet of the scrubber. The optional scrubber has an outlet for liquid connected for instance with the condenser. The reactor and condenser are optionally combined in a single vessel. The condenser is for instance a shell-and-tube heat exchanger with for instance a U-shaped tube bundle.

Figure 2:
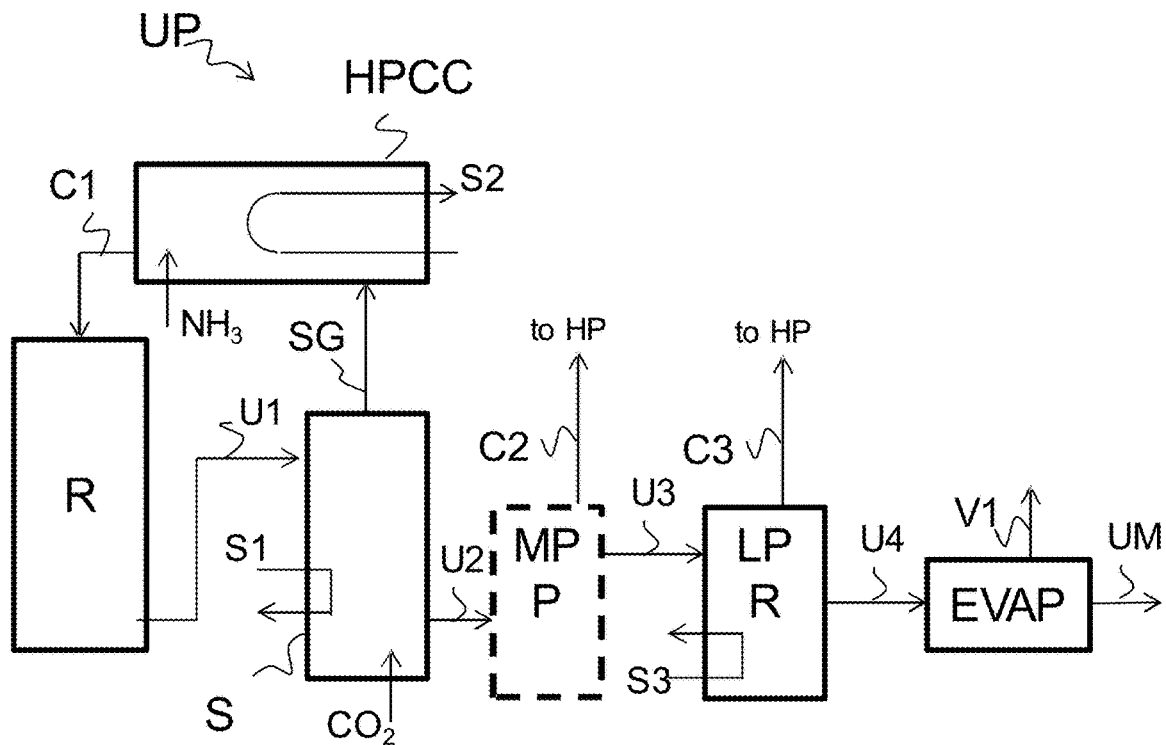
FIG. 2 schematically illustrates an example urea plant according to the invention.

FIG. 2 schematically illustrates a non-limiting example of such a urea. The high pressure section comprises a stripper, preferably as described, a high pressure carbamate condenser (HPCC), a reactor (R), an inlet for $CO_2$ feed and an inlet for $NH_3$ feed. The reactor (R) has an outlet for urea synthesis solution (U1) also comprising carbamate connected with an inlet of the stripper (S), which is for example a $CO_2$ stripper having an inlet for $CO_2$ feed. The stripper has an outlet for mixed gas (SG) and an outlet for stripped urea solution (U2). The gas (SG) is supplied to a high pressure carbamate condenser (HPCC) where it is condensed to carbamate solution (C1) which is supplied to the reactor (R). The carbamate condenser may for instance have an inlet for $NH_3$ feed. The stripper is for instance a shell-and-tube heat exchanger, comprising tubes, for instance comprising the ferritic steel as described and/or other kinds of steel, and uses a heating medium such as steam (S1). In the condenser for instance steam (S2) is raised. The urea plant optionally comprises a medium pressure processing section (MPP) to which stripped urea solution (U2) is supplied and which comprises for instance a decomposer or a flash vessel to give a urea solution (U3) and a gas, and a condenser for said gas to give carbamate solution (C2) which is directly or indirectly recycled to the HP section. The plant further preferably comprises a low pressure recovery section (LPR) having an inlet for stripped urea solution (U2), optionally from said medium pressure processing, and comprising a decomposer using heating (e.g. with steam (S3)) to give purified urea solution (U4) and a gas, and a condenser for said gas to give carbamate solution (C3) which is recycled directly or indirectly to the HP section. The plant optionally further comprises an evaporation section, comprising for instance a vacuum evaporator, receiving purified urea solution (U4), to give a urea melt (UM) and vapor (V1) which is essentially water vapor.

The stripper and urea plant of the invention are preferably suitable for carrying out the urea production process as described. The urea production process as described is preferably carried out using the stripper as described and is preferably carried out in the urea plant as described. Preferences for the urea production process apply equally as preferences for the stripper and for the urea plant. In particular the preferred features for the ferritic steel composition apply equally for the stripper and for the urea plant.

In yet a further embodiment, the urea plant of the invention and/or the urea plant used in the process comprises a HP synthesis section, wherein said HP synthesis section comprises for example a reactor, a stripper and a HP carbamate condenser, and optionally a scrubber, and wherein the HP synthesis section comprises an equipment part made of the mentioned ferritic steel alloy. The equipment part is preferably a component or part of the high pressure carbamate condenser, the reactor, or the scrubber, and for instance is a part of a pool condenser or a pool reactor. Preferably the equipment part is a heat exchanging tube of the condenser, pool condenser, or pool reactor comprised in the HP synthesis section.

The equipment part made of the ferritic steel alloy is for instance a plug, a stem or removable seat of a high pressure control valve, a high pressure check valve or component thereof, a high pressure safety valve or component thereof.

The equipment parts made of the ferritic steel alloy is for instance a valve block for a valve in the HP synthesis section.

The equipment part made of the ferritic steel alloy is for instance a part of an ejector, such as a body of an ejector, wherein the ejector is a high pressure ejector comprised in the HP synthesis section. The HP ejector is e.g. provided in the $NH_3$ feed flow line, or the carbamate recycle flow line, for instance is an ammonia-driven liquid-liquid ejector.

The equipment part made of the ferritic steel alloy is for instance a liquid divider. A liquid divider is for instance a ferrule (e.g. cylinder) with bore holes, which ferrule is adapted to be placed over the tube ends of the stripper. Further preferred features of the liquid divider are as discussed hereinafter.

The invention further pertains to the use of the ferritic stainless steel in ammonium carbamate environment, said use comprising exposing the steel to a fluid comprising ammonium carbamate. The preferred ferritic steels for the process are also preferred for the use.

As used herein, "carbamate" refers to ammonium carbamate.

As used herein, HP is at least 100 bara, e.g. 110-160 bara, MP is 20-60 bara, LP is 4-10 bara, atmospheric is 1-2 bara, for instance 1.0-1.8 bara and sub-atmospheric (LLP) is less than 1.0 bara, e.g. 0.2-0.5 bara; these pressure ranges are for process solutions and not necessarily the same for steam and heating fluids. The abbreviation "bara" means bar absolute.

Bimetallic Tubes

Yet a further aspect of the invention relates to bimetallic tubes and arrangements comprising such tubes, in particular to high pressure strippers of urea plants comprising such tubes.

For good corrosion resistance, low maintenance and long lifetime, the tube-to-tube sheet joints in the stripper are of critical importance.

The stripper is for instance a shell-and-tube heat exchanger comprising a shell, a tube bundle with tubes (typically more than 100 tube or even more than 1000 tubes), and an upper tube sheet and lower tube sheet. The tube sheet is typically a carbon steel plate as pressure bearing part with a corrosion-resistant steel layer (typically applied by overlay welding) at least at the side exposed to urea solution in operation. The stripper tubes are inserted through bore holes drilled in the tube sheet. Each tube is jointed to the tube sheet by welding, in particular to the corrosion resistant weld overlay applied onto the tube sheet. The weld must be of very high quality because this weld has two functions: 1) a strength connection of the tube to the tube sheet and 2) it must completely seal off the bore hole to prevent corrosive ammonium carbamate to come into contact with the carbon steel tube sheet. Welding defects such as for instance pinholes in tube-to-tubesheet joints could cause severe corrosion damage of the pressure retaining carbon-steel tube sheet.

In addition, stripper lifetime is limited by passive corrosion of the stripper tubes. As used herein, passive corrosion refers in practical terms to a corrosion rate of the stainless steel exposed to a corrosive medium of less than 0.30 mm/year.

The present inventors surprisingly found that certain ferritic steel alloys are highly corrosion resistant against carbamate solution, even at high temperatures of more than 200° C. as occurring in stripper tubes and even without the use of added passivating oxygen. Other ferritic stainless steels however perform very poor in ammonium carbamate (even worse than austenitic stainless steels).

U.S. Pat. No. 4,071,083 to Droin describes that the tube of a $CO_2$ stripper of urea plant can be made of a ferritic steel while the cladding (overlay) of the tubesheet is made of an austenitic steel with 18-22% CR, 14-18% Ni, 1-3% Mo and 4-6% Mn. In order to provide a good tube-to-tube sheet joint, the tubes are provided with a ferrule (sleeve) made of austenitic steel and this ferrule is welded to the cladding of the tube sheet. The austenitic steel of the ferrule is 25Cr-22Ni-2Mo which implies that passivation air is used at 0.6 vol. % oxygen in the $CO_2$ feed. Whereas U.S. Pat. No. 4,071,083 mentions that the ferritic steel used resists corrosion by carbamate under stripping conditions, this assumes a high level of passivation air. The document teaches that it is cheaper to produce composite tubes of which only the ferrules are of austenitic steel. For each tube, the joint between the tube and the ferrule is located in the tube sheet which is a disadvantage. In particular the joint is located at the depth of the carbon steel plate. Furthermore, U.S. Pat. No. 4,071,083 does not consider how the urea solution is fed in the tubes.

In the present invention, the stripper is configured for operating with a falling-film of urea solution in the tubes.

To this end, on the upper end of the stripper tubes preferably liquid dividers (also referred to as liquid distributors) are mounted, which are sleeves or ferrules with holes for liquid entry. The liquid dividers are positioned on upper tube ends of the stripper tubes. The upper tube ends protrude from the upper tube sheet. The liquid dividers are for instance provided with a gas tube on top. A background reference on the liquid dividers is US 2012/0282149.

For instance each liquid divider has 3-5 holes in the tube wall of each 2-5 mm diameter. The precise diameter of the holes is important to ensure good liquid film formation. For the purposes of maintenance and inspection, including for tube plugging, it is essential that the liquid dividers can removed. Hence, the tube-to-tube sheet joints do not go through the liquid dividers or sleeves. The liquid dividers are for instance kept in place by a thin sheet with holes through which the ends of the gas stubs of the liquid divers protrudes. The sheet prevents the liquid dividers from falling over or moving in operation of the stripper. The liquid dividers are for instance mounted onto the tube ends using a gasket.

Therefore, there is a need for a way to provide the tube-to-tube sheet joint in case ferritic steel is used for the tubes in the stripper.

Accordingly, the present application in an aspect pertains to a heat exchanger tube that is a bimetallic tube comprising an inner tube layer and an outer tube layer, wherein the inner tube layer is made of a ferritic steel alloy and the outer tube layer is made of a material selected from the group of duplex stainless steel, titanium, titanium alloys, zirconium, zirconium alloys or austenite stainless steel.

For the outer tube layer a duplex ferritic-austenitic stainless steel alloy is preferred. Preferably the inner tube layer is made of the ferritic steel alloy as described herein. Preferably, the inner tube layer and the outer tube layer have a metallurgical bond to each other.

In this way, the joint of the tubes to tube sheet can be made by welding between the outer tube and the overlay of the tube sheet. This may involve welding of two similar steels, e.g. both parts to be welded made of duplex stainless steel. This allows for a reliable weld. In particular, diffusion of N and C into ferritic steel by welding ferritic steel with austenitic steel or duplex stainless steel and the possible resulting increased corrosion risk is avoided.

The inner tube layer and the outer tube layer have a metallurgical bond to each other. This bond is internal inside the tube and is hence not exposed to urea solution. The tube has for instance a total wall thickness of 2-4 mm and each tube layer has a thickness of e.g. 1-3 mm. The inner and outer tube layers are concentric with each other.

The bimetallic tube can be manufactured for instance with methods that are as such known for bimetallic tubes. Other manufacturing methods are also possible.

In one embodiment, the bimetallic tube is manufactured by coextruding the two different alloys into a tube which optionally will be pilgered. For example a ferritic steel sleeve is inserted into a tube and the sleeve and tube are drawn together e.g. with sink drawing.

The two alloys are for instance in the form of a billet. In an embodiment, the manufacture of the bimetallic tube involves hot extrusion of a ferritic steel billet fitted inside a second billet, wherein the second billet is e.g. austenitic or duplex steel. The extruded piece is for instance cold-pilgered to obtain a final diameter and wall thickness.

In a further aspect, the present invention relates to an apparatus, e.g. an arrangement, comprising: at least one steel tube and at least one holder element, wherein the holder element comprises a steel having a duplex austenite-ferrite microstructure or purely austenitic microstructure. The steel tube penetrates the holder element and is attached to the holder element by means of a weld joint provided on an outer surface of the tube and on the holder element. The steel tube is a compound tube, comprising an inner tube part which has a purely ferritic microstructure, and an outer tube part which has a duplex austenite-ferrite microstructure or purely austenitic microstructure.

Thereby, due to the fact that a duplex austenite-ferrite microstructure or purely austenitic microstructure has a better weldability than a purely ferritic microstructure, a strong and reliable weld joint can be achieved without any need of post heat treatment of the tube in the region of the weld, which would have been necessary if the tube only had comprised a ferritic microstructure.

According to one embodiment, the apparatus comprises means for introduction of corrosive media into the tube, and means for heating the tube from outside. In an embodiment, the inner tube part comprises ferritic steel having a first corrosion resistance to a corrosive medium and the outer tube part comprises a duplex austenite-ferrite microstructure or purely austenitic steel having a second corrosion resistance to the same corrosive media, wherein the first corrosion resistance of the ferritic steel is higher than the second corrosion resistance at the elevated temperatures (such as in the range 180-230° C.) caused by the means for heating the tube from the outside. The means for introduction of corrosive media into the tubes are for instance an inlet. The means for heating the tube from the outside are for instance a shell encompassing the tubes which are arranged in a tube bundle, wherein the shell has an inlet for steam and an outlet for steam and/or condensate.

For instance, the corrosive media is media for which the ferritic steel has higher corrosion resistance than has said duplex austenite-ferrite microstructure or purely austenitic microstructure at the elevated temperatures caused by the means for heating the tube from outside.

Preferably, the ferritic material has superior corrosion properties (better than those of the steel of the outer tube part) in an ammonia carbamate environment such as are present in a urea plant. The ferritic material can be used at lower oxygen pressures (even without addition or air to the process) and high temperatures with lower corrosion rates than measured for the steel grade of the outer tube part.

According to yet another embodiment, the corrosive media comprises a mixture of water, urea and ammonium carbamate.

According to one embodiment the outer tube part consists of a duplex stainless steel with more than 25% chromium, 4-9% Ni, 1-5% Mo, and low impurity levels, for example UNS S32906. It is also possible to use an austenitic stainless steel, for example UNS S31050.

Figure 3:
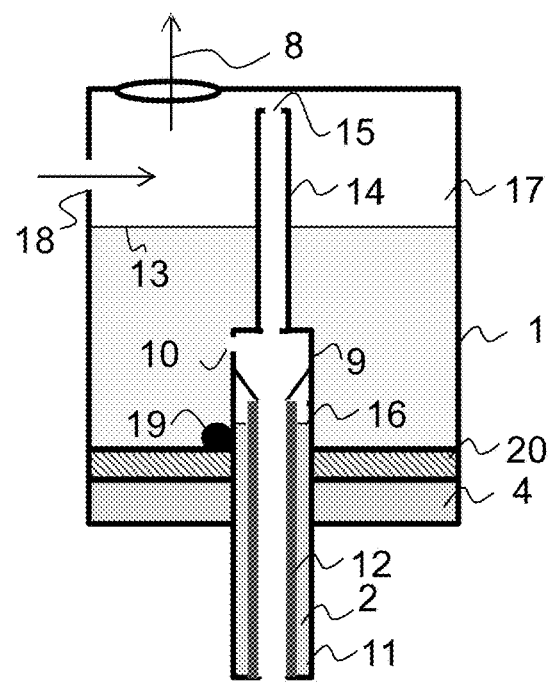
FIG. 3 schematically illustrates another example stripper according to the invention.

An example of an apparatus according to the invention, here embodied by a so-called stripper, is shown in FIG. 3.

The function or the stripper is to separate urea from the corrosive intermediate ammonium carbamate. The process fluid that enters the stripper is a mixture of water, urea, and ammonium carbamate. The stripper is a standing tube and sheet heat exchanger with one ferrule on each heat exchanger tube. The ferrule controls the liquid flow and distribution entering each tube. During normal operation a liquid film is created on the inner surface of the heat exchanger tubes. The stripping is performed by heat and is assisted by a stripping gas (for example $CO_2$). When the carbamate solution is heated the carbamate is decomposed to ammonia and carbon dioxide in gas phase. The water and urea exit the stripper in the bottom as liquid (from the bottom chamber), and the process gases exit from the top of the stripper, in particular from the top chamber.

In a preferred embodiment, the apparatus, preferably the stripper, comprises a tube penetrating the holder element (which is for instance a tube sheet). A liquid distributor made from the same material as the outer tube (e.g. steel S32906) consists of a cylinder with bore holes placed over the tube ends. The bore holes allow the process fluid (urea and ammonium carbamate containing aqueous stream) to enter the tube.

FIG. 3 shows an example inventive apparatus, in particular an example urea stripper, with the tube (2) penetrating the holder element (illustrated as a tube sheet (4)) and having a protruding tube end (16). The tube (2) is a compound tube comprising an outer tube part (11) and an inner tube part (12). A liquid distributor (9) is for example made from the same material as the outer tube part (11) (for instance UNS S32906) and consists for example of a cylinder with bore holes (10). The liquid distributor (9) is placed over the tube ends (16). The bore holes allow the process fluid (urea and ammonium carbamate containing aqueous stream) to enter the tube and be in contact with the inner tube part (12) during the stripping. The inner tube part (12) has a purely ferritic microstructure and is made of ferritic steel, preferably of a ferritic steel alloy as discussed. In operation of the stripper, the liquid level (13) of the urea solution in the upper chamber (17) is maintained above the bore holes (10). The upper chamber (17) comprises the inlet for urea solution (18). In the chamber (17), also a weld (19) is provided between the outer tube part (11), in particular the protruding end part thereof, and an overlay (20) of the upper tube sheet (4).

Optionally a gas tube (14) is mounted on the liquid distributor (9). The gas tube has an outlet (15) for gas which in operation of the apparatus is arranged above the liquid level (13).

An advantage of this embodiment is that the outer tube material is has good resistance to corrosion in ammonium carbamate containing environments, in particular at the (relatively lower) temperatures occurring in the bottom chamber and the top chamber. Therefore no specific measures need to be taken to connect the inner and outer tube together, for instance an omega-bond connection is not necessary. The same advantage applies for the embodiments of the process, stripper and plant wherein the outer tube material comprises austenitic steel or austenitic-ferritic stainless steel.

Manufacturing Method

In yet a further aspect the invention pertains to a manufacturing method for bimetallic components, in particular heat exchanging tubes.

The present inventors surprisingly found that certain ferritic steel alloys are highly corrosion resistant against carbamate solution, even at high temperatures of more than 200° C. (e.g. in the range of 205 to 220° C.) and even in (essentially) oxygen-free carbamate solutions.

However, for using equipment parts comprising or made of such ferritic steel alloys in urea plants, the equipment part must be joined together to other parts of the units and sections of the urea plant. Typically welding is used for joining steel parts. However, achieving a high quality weld which does not affect corrosion resistance is challenging for ferritic stainless steels, in particular for welds of ferritic stainless steels to austenitic steels or to duplex stainless steels. There is a risk of diffusion of N and C into the ferritic steel when welding it to austenitic steel or duplex stainless steel having a higher N or C content and this may cause increased corrosion risk.

Hence there is a need for equipment parts of urea plants comprising ferritic steel alloys which can be better joined, in particular can be better joined to equipment parts made of other types of steel such as austenitic steel and duplex stainless steel.

The present invention pertains in an aspect to a method of manufacturing a component, preferably for a urea plant, wherein the component comprises a first and a second part which have a metallurgical bond to each other, wherein the first part is made of ferritic stainless steel, and the second part is for instance made of a different type of steel than the first part, for instance wherein the second part is made of austenitic or duplex stainless steel, the method comprising:

i) providing a mold defining the shape of an object to be manufactured:

ii) filling a portion of the mold corresponding to said first part with first stainless steel alloy powder which is a ferritic stainless steel alloy powder;

iii) filling a portion of the mold corresponding to said second part with a second stainless steel alloy powder having a different elemental composition than said first stainless steel alloy powder:

iv) subjecting said mold, as filled with said first and second stainless steel alloy powder to hot isostatic pressing (HIP), to give a consolidated object.

The HIP for instance involves submitting the mold, as filled, to a predetermined temperature and predetermined pressure for a predetermined time so that the particles of the powders bond metallurgically to each other to produce the object. The temperature is below the melting point of the alloy and is e.g. above 500° C. or above 900° C. The pressure is e.g. above 500 bar or above 900 bar. The time is e.g. at least 30 minutes or at least 60 minutes. The pressure is applied as isostatic fluid pressure, in particular isostatic gas pressure. The mold is for instance a container. The container is for instance placed in a pressure furnace during the HIP stage and for instance argon is used as pressure gas in the furnace. The container material is for instance malleable at the HIP temperature. The container is for example leak proof at the HIP pressures.

The filling step comprises for instance a step of applying vacuum to remove air from the mold. The filling step comprises for instance a step of closing and sealing the mold or container.

US 2018/0304224 describes objects made by hot isostatic pressing (HIP) of ferritic-austenitic steel alloys. In an embodiment of the present invention, the HIP as used in the present manufacturing method is similar to the one used in US 2018/0304224.

The steel alloy powder is for instance obtained by atomization of hot alloy. The powder for example consists of particles with a particle size distribution with the $D_{50}$ in the range of 80-130 μm Preferably the method further comprises releasing the consolidated object from the mold or removing the mold from the object. The method further optionally comprises machining or drilling the consolidated object, e.g. to form holes in it. The consolidated object may also already provide the component directly without need for further machining or drilling.

In embodiments wherein the manufactured component is a part of a urea plant, the first part comprises a surface which in operation is exposed to for instance carbamate-containing solution. Advantageously the second part can be used for welding e.g. to a second component. The second component is made for instance, at the weld spot, of austenitic or duplex steel. For instance the second component and the second part are made of the same type of steel. The second part comprises for example an external surface of the component.

The component is for instance a bimetallic stripper tube with the first part being an inner tube layer and the second part being an outer tube layer.

Preferably the first part is made of the ferritic steel alloy as described herein, for instance according to Preferred Alloy Compositions 1-3 described herein.

The invention also pertains to a component, in particular for a urea plant, comprising a first part and a second part metallurgically bonded together, wherein the first part is made of ferritic steel, preferably the mentioned ferritic steel, and wherein the second part is for instance made of austenitic or duplex stainless steel. The component is for instance a stripper tube as described. The invention also pertains to a stripper comprising such a stripper tube. The stripper is for instance a shell-and-tube heat exchanger, with the falling-film configuration as described. The component is for instance obtainable by the HIP method as described. The second part is for instance made of duplex stainless steel having a isotropic microstructure.

EXAMPLES

The invention will now be further illustrated by the following non-limiting examples.

Example 1

Corrosion tests of several grades ferritic stainless steels (FSS) in oxygen free ammonium-carbamate were carried out. The performance is compared with a duplex stainless steel grade (DSS-01) and an austenitic stainless steel grade (ASS-05) as reference. The corrosion tests were conducted in a high pressure autoclave containing concentrated ammonium-carbamate at 210° C. without passivation air (zero oxygen). The compositions (in wt. %, balance Fe) and the results are shown in Table 1. The ferritic steel FSS-90 containing more than 50 ppm Nb, C less than 50 ppm and N less than 125 ppm gave a corrosion rate even lower than that of the reference duplex stainless steel. The very low corrosion rate, for passive corrosion, of 0.11 mm/year in the said corrosion test of the ferritic steel FSS-90 compared to the reference DSS-01 (0.22 mm/y) indicates an expected lifetime of the stripper containing said FSS-90 tubes of more than 20 year even without the use of passivation air compared to an expected lifetime of 15-18 years for existing strippers and stripper tubes.

TABLE 1

| Sample | C | Si | Mn | Cr | Ni | N | P | S | Mo | Nb | Rate: mm/y |
|---|---|---|---|---|---|---|---|---|---|---|---|
| FSS-79 | 0.007 | 0.59 | 0.69 | 26.65 | 0.36 | 0.02 | | | — | — | 5.50 |
| FSS-84 | 0.1 | 0.43 | 0.63 | 26.87 | 0.31 | 0.18 | | | — | — | 4.54 |
| FSS-90 | 0.002 | 0.20 | 0.05 | 26.00 | 0.15 | 0.01 | 0.010 | 0.011 | 1 | 0.11 | 0.11 |
| FSS-29 | 0.019 | 0.55 | 0.36 | 28.53 | 0.50 | 0.026 | 0.023 | <0.0005 | 3.63 | 0.35 | 0.42 |
| ASS-05 | 0.02 | 0.35 | 1.50 | 24.9 | 21.5 | 0.13 | | | 2.10 | — | 5.69 |
| DSS-01 | 0.029 | 0.45 | 1.25 | 28.3 | 6.20 | 0.35 | | | 2.10 | — | 0.22 |

The invention claimed is:

1. A method of manufacturing a component, wherein the component comprises a first and a second part which have a metallurgical bond to each other, wherein the first part is made of ferritic stainless steel, and the second part is made of a different type of steel than the first part, the method comprising: i) providing a mold defining the shape of an object to be manufactured; ii) filling a portion of the mold corresponding to said first part with first stainless steel alloy powder which is a ferritic stainless steel alloy powder; iii) filling a portion of the mold corresponding to said second part with a second stainless steel alloy powder having a different elemental composition than said first stainless steel alloy powder; and iv) subjecting said mold, as filled with said first and second stainless steel alloy powder, to hot isostatic pressing, to give a consolidated object.

2. The method according to claim 1, wherein the component is a component of a urea plant.

3. The method according to claim 2, wherein the first part has a purely ferritic microstructure and wherein the second part is made of austenitic or duplex stainless steel.

4. The method according to claim 3, wherein the component is a bimetallic stripper tube, wherein the first part is an inner tube layer and the second part is an outer tube layer.

5. The method according to claim 1, wherein the ferritic stainless steel comprises in weight %:
C max. 0.005;
Si 0.1 to 0.4;
Mn max. 0.4;
P max. 0.020;
S max. 0.020;
Cu max. 0.25;
Ni max. 0.50;
Cr 20.0 to 35.0;
Mo 0.75 to 1.50;
N 0.0050 to 0.0125; and
Nb 0.060 to 0.375;
balance Fe, max. 0.50 wt. % total added processability elements, and impurities, and wherein the amount of Nb in wt. % meets the following equation $12*(\text{wt. \% N}) < Nb < 30*(\text{wt. \% N})$.

6. The method according to claim 5, wherein the amount of Nb in wt. % meets the equation $15*(\text{wt. \%}) N < Nb < 25*(\text{wt. \% N})$.

7. The method according to claim 5, wherein the ferritic stainless steel comprises in weight %:
C max. 0.0030.

8. The method according to claim 5, wherein the ferritic stainless steel comprises in weight %:
Si 0.1 to 0.3.

9. The method according to claim 5, wherein the ferritic stainless steel comprises in weight %:
Mn max. 0.2.

10. The method according to claim 5, wherein the ferritic stainless steel comprises in weight %:
Ni max. 0.20.

11. The method according to claim 5, wherein the ferritic stainless steel comprises in weight %:
Cr 25.0 to 27.5.

12. The method according to claim 1, wherein the ferritic stainless steel comprises:
C max. 0.0030
Si 0.1 to 0.3
Mn max. 0.2
P max. 0.020
S max. 0.020
Cu max. 0.25
Ni max. 0.20
Cr 25.0 to 27.5
Mo 0.75 to 1.50
N 0.0050 to 0.0125
Nb 0.060 to 0.375
balance Fe and unavoidable occurring impurities; and wherein the amount of Nb in wt. % meets the following equation $12*(\text{wt. \% N}) < Nb < 30*(\text{wt. \% N})$.

13. The method according to claim 12, wherein the amount of Nb in wt. % meets the equation $15*(\text{wt. \%}) N < Nb < 25*(\text{wt. \% N})$.

14. The method according to claim 1, wherein the hot isostatic pressing is performed at a temperature below the melting point of said first and second stainless steel alloy powder.

15. The method according to claim 14, wherein the temperature is above 500° C.

16. The method according to claim 15, wherein the temperature is above 900° C.

17. The method according to claim 1, wherein said first and second stainless steel alloy powder consist of particles with a particle size distribution with a $D_{5o}$ in the range of 80-130 μm.

* * * * *